United States Patent [19]
Braxton et al.

[11] Patent Number: 5,955,284
[45] Date of Patent: Sep. 21, 1999

[54] ASSAY METHOD TO DETECT SERPIN DERIVED FROM HUMAN HYPOTHALAMUS

[75] Inventors: Scott Michael Braxton, San Mateo; Dinh Diep, San Francisco; Susan G. Stuart, Montara, all of Calif.

[73] Assignee: Incyte Pharmaceuticals, Inc., Palo Alto, Calif.

[21] Appl. No.: 09/203,237

[22] Filed: Dec. 1, 1998

Related U.S. Application Data

[62] Division of application No. 08/997,040, Dec. 23, 1997, which is a division of application No. 08/487,823, Jun. 7, 1995, Pat. No. 5,700,924.

[51] Int. Cl.$^6$ .............................. C12Q 1/68; C07H 21/04
[52] U.S. Cl. .......................... 435/6; 536/23.1; 536/24.31
[58] Field of Search ............................... 435/6; 536/23.1, 536/24.31

[56] References Cited

PUBLICATIONS

Loebermann et al., "Human $\alpha_1$–Proteinase Inhibitor, Crystal Structure Analysis of Two Crystal Modifications, Molecular Model and Preliminary Analysis of the Implications for Function," *J. Mol. Biol.* 177:531–556 (1984).

Bruch et al., "Plasma Serine Proteinase Inhibitors (Serpins) Exhibit Major Conformational Changes and a Large Increase in Conformational Stability upon Cleavage at Their Reactive Sites," *J. Biol. Chem.* 263(32):16626–16630 (Nov. 15, 1988).

Carrell et al., "Serpins: mobile conformation in a family of proteinase inhibitors," *Curr. Opin. Struct. Biol.* 2(3):438–446 (Jun. 1992).

Mottonen et al., "Structural basis of latency in plasminogen activator inhibitor–1," *Nature* 355(6357):270–273 (Abstract only) (Jan. 16, 1992).

Pemberton et al., "Hormone binding globulins undergo serpin conformational change in inflammation," *Nature* 336:257–258 (Nov. 17, 1988).

Carrell et al., "$\alpha_1$–Antitrypsin and the serpins: variation and countervariation," *TIBS* 10:20–24 (Jan. 1985).

Carrell et al., "The Serpins: Evolution and Adaptation in a Family of Protease Inhibitors," *Cold Spring Harbor Symp. Quant. Biol.* 52:527–535 (1987).

Huber et al., "Implications of the Three–Dimensional Structure of $\alpha_1$–Antitrypsin for Structure and Function of Serpins," *Biochemistry* 28(23):8951–8966 (Nov. 14, 1989).

Remold–O'Donnell, E., "The ovalbumin family of serpin proteins," *FEBS* 315(2):105–108 (Abstract only) (Jan. 4, 1993).

Morris, J.F., "New anatomical insights into the inputs and outputs from hypothalamic magnocellular neurons," *Ann NY Acad. Sci.* 689:16–33 (Abstract only) (Jul. 22, 1993).

Renaud et al., "Synapic and neurotransmitter regulation of activity in mammalian hyptothalamic magnocellular neurosecretory cells," *Prog. Brain Res.* 92:227–288 (Abstract only) (1992).

Erlander et al., "Molecular approach to hypothalamic rhythms: isolation of novel indoleamine receptor genes," *J. Biol. Rhythms* 8 Suppl, pp. 25–31 (Abstract only) (1993).

Braak et al., "Anatomy of the human hypothalamus (chiasmatic and tuberal region)," *Prog. Brain Res.* 93:3–14, discussion pp. 14–16 (Abstract only) (1992).

Swaab et al., "Functional neuroanatomy and neuropathology of the human hypothalamus," *Anat. Embryol.* 187(4):317–330 (Abstract only) (Apr. 1993).

GenBank Sequence Database (Accession No. Z71930), National Center for Biotechnology Information, National Library of Medicine, Bethesda, Maryland 20894 1996.

Osterwalder et al., Neuroserpin, an axonally secreted serine protease inhibitor, *The Embo Journal*, 15(12):2944–2953 (1996).

San, H., et al., Safety and Short Term Toxicity of a Novel and Cationic Formulation for Human Gene Therapy, Human Gene Therapy, 781–788 (1993).

Christoffersen, R., et al., Ribozymes as Human Therapeutic Agents, *Journal of Medicinal Cheistry*, 2023–2037 (1994).

Stull, R., et al., Antigene, Ribozyme, and Aptomer Nucleic Acid Drugs: Progress and Prospects, Pharmaceuticals Research (1995).

Ngo et al., Computational complexity, protein structure prediction, and the Levinthal Paradox, The Protein Folding Problem and Tertiary Structure Prediction, pp. 433–440 (1994).

Wu et al., Molecular cloning and cell free expression of mouse antithrombin III, Throm. Haemost, vol. 38 (3), pp. 291–296.

*Primary Examiner*—Nancy Degen
*Assistant Examiner*—Andrew Wang
*Attorney, Agent, or Firm*—Sheela Mohan-Peterson; Incyte Pharmaceuticals, Inc.

[57] ABSTRACT

The present invention provides nucleotide and amino acid sequences that identify and encode a novel serpin (CAPE) expressed in human hypothalamus. The present invention also provides for antisense molecules to the nucleotide sequences which encode CAPE, expression vectors for the production of purified CAPE, antibodies capable for binding specifically to CAPE, hybridization probes or oligonucleotides for the detection of CAPE-encoding nucleotide sequences, genetically engineered host cells for the expression of Cape, a pharmaceutical composition containing biologically active CAPE, a diagnostic test based on CAPE-encoding nucleic acid molecules, and treatment methods comprising administration of biologically active CAPE.

1 Claim, 7 Drawing Sheets

```
                    9              18             27             36             45          54
5' AAT TCG GCA CGA GGG AAA GGA GAG GAA GGG GGG GGC AAG CCC TCA CCT GCG CCA 63             72             81             90             99          108
   ATC AGG GTT TGA AAC TGT TAC AAT ATG GCT TTC CTG GGA CTC TTC TCT TTG CTG
                                       M   A   F   L   G   L   F   S   L   L 117            126            135            144            153         162
   GTT CTG CAG AGT ATG GCT ACA GGG GCC ACT TTC CCT GAG GAA GCC ATT GTT GAC
    V   L   Q   S   M   A   T   G   A   T   F   P   E   E   A   I   V   D 171            180            189            198            207         216
   TTG TCA GTG AAT ATG TAT AAT CGT CTT AGA GCC ACT GGT GAA GAT GAA AAT ATT
    L   S   V   N   M   Y   N   R   L   R   A   T   G   E   D   E   N   I 225            234            243            252            261         270
   CTC TTC TCT CCA TTG AGT ATT GCT CTT GCA ATG GGA ATG ATG GAA CTT GGG GCC
    L   F   S   P   L   S   I   A   L   A   M   G   M   M   E   L   G   A 279            288            297            306            315         324
   CAA GGA TCT ACC CAG AAA GAA ATC CGC CAC TCA ATG GGA TAT GAC AGC CTA AAA
    Q   G   S   T   Q   K   E   I   R   H   S   M   G   Y   D   S   L   K 333            342            351            360            369         378
   AAT GGT GAA GAA TTT TCT TTC TTG AAG GAG TTT TCA AAC ATG GTA ACT GCT AAA
    N   G   E   E   F   S   F   L   K   E   F   S   N   M   V   T   A   K 387            396            405            414            423         432
   GAG AGC CAA TAT GTG ATG AAA ATT GCC AAT TCC TTG TTT GTG CAA AAT GGA TTT
    E   S   Q   Y   V   M   K   I   A   N   S   L   F   V   Q   N   G   F 441            450            459            468            477         486
   CAT GTC AAT GAG GAG TTT TTG CAA ATG ATG AAA AAA TAT TTT AAT GCA GCA GTA
    H   V   N   E   E   F   L   Q   M   M   K   K   Y   F   N   A   A   V 495            504            513            522            531         540
   AAT CAT GTG GAC TTC AGT CAA AAT GTA GCC GTG GCC AAC TAC ATC AAT AAG TGG
    N   H   V   D   F   S   Q   N   V   A   V   A   N   Y   I   N   K   W 549            558            567            576            585         594
   GTG GAG AAT AAC ACA AAC AAT CTG GTG AAA GAT TTG GTA TCC CCA AGG GAT TTT
    V   E   N   N   T   N   N   L   V   K   D   L   V   S   P   R   D   F 603            612            621            630            639         648
   NAT GCT GCC ACT TAT CTG GCC CTC ATT AAT GCT GTC TAT TTC AAG GGG AAC TGG
    X   A   A   T   Y   L   A   L   I   N   A   V   Y   F   K   G   N   W 657            666            675            684            693         702
   AAG TCG CAG TTT AGG CCT GAA AAT ACT AGA ACC TTT TCT TTC ACT AAA GAT GAT
    K   S   Q   F   R   P   E   N   T   R   T   F   S   F   T   K   D   D 711            720            729            738            747         756
   GAA AGT GAA GTC CAA ATT CCA ATG ATG TAT CAG CAA GGA GAA TTT TAT TAT GGG
    E   S   E   V   Q   I   P   M   M   Y   Q   Q   G   E   F   Y   Y   G
```

FIGURE 1A

```
              765           774           783           792           801           810
GAA TTT AGT GAT GGC TCC AAT GAA GCT GGT GGT ATC TAC CAA GTC CTA GAA ATA
 E   F   S   D   G   S   N   E   A   G   G   I   Y   Q   V   L   E   I 819           828           837           846           855           864
CCA TAT GAA GGA GAT GAA ATA AGC ATG ATG CTG GTG CTG TCC AGA CAG GAA GTT
 P   Y   E   G   D   E   I   S   M   M   L   V   L   S   R   Q   E   V 873           882           891           900           909           918
CCT CTT GCT ACT CTG GAG CCA TTA GTC AAA GCA CAG CTG GTT GAA GAA TGG GCA
 P   L   A   T   L   E   P   L   V   K   A   Q   L   V   E   E   W   A 927           936           945           954           963           972
AAC TCT GTG AAG AAG CAA AAA GTA GAA GTA TAC CTG CCC AGG TTC ACA GTG GAA
 N   S   V   K   K   Q   K   V   E   V   Y   L   P   R   F   T   V   E 981           990           999          1008          1017          1026
CAG GAA ATT GAT TTA AAA GAT GTT TTG AAG GCT CTT GGA ATA ACT GAA ATT TTC
 Q   E   I   D   L   K   D   V   L   K   A   L   G   I   T   E   I   F 1035          1044          1053          1062          1071          1080
ATC AAG ATC AAA TTT GAC AGC CTC TCT GAT AAT AAG GAG ATT TTT CTT TCC AAA
 I   K   I   K   F   D   S   L   S   D   N   K   E   I   F   L   S   K 1089          1098          1107          1116          1125          1134
GCA ATT CAC AAG TCC TTC CTA GAG GTT AAT GAA GAA GGC TCA GAA CTC TCT GTC
 A   I   H   K   S   F   L   E   V   N   E   E   G   S   E   L   S   V 1143          1152          1161          1170          1179          1188
TCA GGA ATG ATT CAA TTA GTA GGA TGC TGT CTG TAT CCT CAA GTT ATT GTC GAC
 S   G   M   I   Q   L   V   G   C   C   L   Y   P   Q   V   I   V   D 1197          1206          1215          1224          1233          1242
CAT CCA TTT TTC TTT CTT ATC AGA AAC AGG AGA ACT GGT ACA ATT CTA TTC ATG
 H   P   F   F   F   L   I   R   N   R   R   T   G   T   I   L   F   M 1251          1260          1269          1278          1287          1296
GGA CGA GTC ATG CAT CCT GAA ACA ATG AAC ACA AGT GGA CAT GAT TTC GAA GAA
 G   R   V   M   H   P   E   T   M   N   T   S   G   H   D   F   E   E 1305          1314          1323          1332          1341          1350
CTT TAA GTT ACT TTA TTT GAA TAA CAA GGA AAA CAG TAA CTA AGC ACA TTA TGT
 L 1359          1368          1377          1386          1395          1404
TTG CAA CTG GTA TAT ATT TAG GAT TTG TGT TTT ACA GTA TAT CTT AAG ATA ATA 1413          1422          1431          1440          1449          1458
TTT AAA ATA GTT CCA GAT AAA AAC AAT ATA TGT AAA TTA TAA GTA ACT TGT CAA 1467          1476          1485          1494          1503          1512
GGA ATG TTA TCA GTA TTA AGC TAA TGG TCC TGT TAT GTC ATT GTG TTT GTG TGC 1521          1530          1539          1548          1557
TGT TGT TTA AAA TAA AAG TAC CTA TTG AAA AAA AAA AAA AAA AAA A 3'
```

FIGURE 1B

```
              M A F L G L F S L L V L E S L A V G A T L P E E A I V D L A   Majority
                         10                  20                  30
  1   M A F L G L F S L L V L Q S M A T G A T F P E E A I V D L S   84476
  1   M - - - - - - - - - - - E D L C V A N T L - - - - - - - F A   PAI-2

V N L F N H L A A A G E T E N L L L S P L S I A L A M G M V   Majority
                         40                  50                  60
 31   V N M Y N R L R A T G E D E N I L F S P L S I A L A M G M M   84476
 13   L N L F K H L A K A S P T Q N L F L S P W S I S S T M A M V   PAI-2

E L G A Q G S T E D E I A K V L G F D S V G A N A V T P K T   Majority
                         70                  80                  90
 61   E L G A Q G S T Q K E I R H S M G Y D S L - - - - - - - K N   84476
 43   Y M G S R G S T E D Q M A K V L Q F N E V G A N A V T P M T   PAI-2

G E E F S S C G F L Q E I Q K G S Y P D A I L Q A Q A A D K   Majority
                        100                 110                 120
 84   G E E F S - - - F L K E - - - - - - - - - - - - - - - - - -   84476
 73   P E N F T S C G F M Q Q I Q K G S Y P D A I L Q A Q A A D K   PAI-2

I H S S F S S L S S A V T A S T G N Y V L E I A N S L F G E   Majority
                        130                 140                 150
 93   - - - - - F S N M - - - V T A K E S Q Y V M K I A N S L F V Q   84476
103   I H S S F R S L S S A I N A S T G N Y L L E S V N K L F G E   PAI-2

N G A S V N E E F L Q L C Q K Y F S A A V N A V D F L E N A   Majority
                        160                 170                 180
116   N G F H V N E E F L Q M M K K Y F N A A V N H V D F S Q N V   84476
133   K S A S F R E E Y I R L C Q K Y S S E P Q A V D F L E C A   PAI-2

A V A R N K I N S W V E T N T N G L V K D L V S E G S V X G   Majority
                        190                 200                 210
146   A V A - N Y I N K W V E N N T N N L V K D L V S P R D F X A   84476
163   E E A R K K I N S W V K T Q T K G K I P N L L P E G S V D G   PAI-2

A T R L A L V N A V Y F K G N W K S Q F E K E L T G L F S F   Majority
                        220                 230                 240
175   A T Y L A L I N A V Y F K G N W K S Q F R P E N T R T F S F   84476
193   D T R M V L V N A V Y F K G K W K T P F E K K L N G L Y P F   PAI-2
```

FIGURE 2A

```
            T V D S A S E V Q V Q M M Y L Q G E L N I G E F I D G L N A   Majority
                              250              260             270
        205 |T K D D E S E V Q I|P M M Y|Q Q|G E F|Y Y|G E F S D G S N E| 84476
        223  R V N S A Q R T P V Q|M M Y|L R E K L N I|G|- Y I E D L K A  PAI-2

A G G I Y Q V L E L P Y A G D E V S M F L V L S D E I A D V   Majority
                              280              290             300
        235 |A G G I Y Q V L E I P Y E G D E I S M M L V L S R Q E V P L| 84476
        252  - - - - -|Q I|L E|L P Y|A|G D|- V|S M F|L|L L|P D E I A D V  PAI-2

A T G L E L L E S L V T A D L V E E W A S S V K K A E D E V   Majority
                              310              320             330
        265 |A T|- - - -|L E|P L V K A Q L V E E W|A N S V K K|- -|Q K V| 84476
        276  S|T|G L E L|L E|S E I T Y D K L N K|W|T S K D|K|M A E D E|V| PAI-2

E V Y L P Q F T V E E E I D L K S V L K A L G I T D A F I K   Majority
                              340              350             360
        289 |E V Y L P R F T V E Q E I D L K D V L K A L G I T E I F I K| 84476
        306 |E V Y|I|P Q|F|K L|E|E H Y E|L|R S I|L|R S M|G|M E D A F|N K| PAI-2

G K A N F S G L S D N N D L F L S E A I H Q A F V D V N E E   Majority
                              370              380             390
        319 |I K|- -|F D S L S D N K E I F L S K A I H K S F L E V N E E| 84476
        336  G R A N|F|S G M|S|E R N D L|F L S|E V F|H|Q A M V D|V N E E| PAI-2

G S E A A A G G G G V L V G R T G H G G P Q V V A D H P F L   Majority
                              400              410             420
        347 |G S E L S V S G M I Q L V G C C L Y|- -|P Q V I V D H P F F| 84476
        366 |G T|E|A A A G T G G V M T|G|R T G H G G|P Q|F V A|D H P F|L  PAI-2

F L I R N K I T G T I L F F G R V M H P E T M N T S G H D F   Majority
                              430              440             450
        375 |F L I|R N R R|T G T I L F|M|G R V M H P E T M N T S G H D F| 84476
        396 |F L I|M H K I|T|N C|I L F|F|G R|- - - - - - - - - - - - - F| PAI-2

S S L                                                         Majority

405 |E E L|                                                       84476
        413  S S P                                                        PAI-2
```

FIGURE 2B

```
       M A T G A V F P E E A I V L L A V N L F N H L A A A G E T E   Majority
                      10              20              30
 1     M A T G A T F P E E A I V D L S V N M Y N R L R A T G E D E   84476
 1     M E D L C V - - - - A N T L F A L N L F K H L A K A S P T Q   PAI-2

N L L L S P L S I A L A M G M V E L G A Q G S T E D E I A K   Majority
                      40              50              60
31     N I L F S P L S I A L A M G M M E L G A Q G S T Q K E I R H   84476
27     N L F L S P W S I S S T M A M V Y M G S R G S T E D Q M A K   PAI-2

V L G F D S V G A N A V T P K T G E E F S S C G F L Q E I Q   Majority
                      70              80              90
61     S M G Y D S L - - - - - - - K N G E E F S - - - F L K E - -   84476
57     V L Q F N E V G A N A V T P M T P E N F T S C G F M Q Q I Q   PAI-2

K G S Y P D A I L Q A Q A A D K I H S S F S S L S S A V T A   Majority
                      100             110             120
79     - - - - - - - - - - - - - - - - - - - F S N M - - - V T A   84476
87     K G S Y P D A I L Q A Q A A D K I H S S F R S L S S A I N A   PAI-2

S T G N Y V L E I A N S L F G E N G A S V N E E F L Q L C Q   Majority
                      130             140             150
86     K E S Q Y V M K I A N S L F V Q N G F H V N E E F L Q M M K   84476
117    S T G N Y L L E S V N K L F G E K S A S F R E E Y I R L C Q   PAI-2

K Y F S A A V N A V D F L E N A A V A R N K I N S W V E T N   Majority
                      160             170             180
116    K Y F N A A V N H V D F S Q N V A V A - N Y I N K W V E N N   84476
147    K Y Y S S E P Q A V D F L E C A E E A R K K I N S W V K T Q   PAI-2

T N G L V K D L V S E G S V X G A T R L A L V N A V Y F K G   Majority
                      190             200             210
145    T N N L V K D L V S P R D F X A A T Y L A L I N A V Y F K G   84476
177    T K G K I P N L L P E G S V D G D T R M V L V N A V Y F K G   PAI-2

N W K S Q F E K E L T G L F S F T V D S A S E V Q V Q M M Y   Majority
                      220             230             240
175    N W K S Q F R P E N T R T F S F T K D D E S E V Q I P M M Y   84476
207    K W K T P F E K K L N G L Y P F R V N S A Q R T P V Q M M Y   PAI-2
```

FIGURE 2C

```
        L Q G E L N I G E F I D G L N A A G G I Y Q V L E L P Y A G   Majority
                         250               260               270
205     Q Q G E F Y Y G E F S D G S N E A G G I Y Q V L E I P Y E G   84476
237     L R E K L N I G - Y I E D L K A - - - - - Q I L E L P Y A G   PAI-2

D E V S M F L V L S D E I A D V A T G L E L L E S L V T A D   Majority
                         280               290               300
235     D E I S M M L V L S R Q E V P L A T - - - - L E P L V K A Q   84476
261     D - V S M F L L L P D E I A D V S T G L E L L E S E I T Y D   PAI-2

L V E E W A S S V K K A E D E V E V Y L P Q F T V E E E I D   Majority
                         310               320               330
261     L V E E W A N S V K K - - Q K V E V Y L P R F T V E Q E I D   84476
290     K L N K W T S K D K M A E D E V E V Y I P Q F K L E E H Y E   PAI-2

L K S V L K A L G I T D A F I K G K A N F S G L S D N N D L   Majority
                         340               350               360
289     L K D V L K A L G I T E I F I K I K - - F D S L S D N K E I   84476
320     L R S I L R S M G M E D A F N K G R A N F S G M S E R N D L   PAI-2

F L S E A I H Q A F V D V N E E G S E A A A G G G V L V G     Majority
                         370               380               390
317     F L S K A I H K S F L E V N E E G S E L S V S G M I Q L V G   84476
350     F L S E V F H Q A M V D V N E E G T E A A A G T G G V M T G   PAI-2

R T G H G G P Q V V A D H P F L F L I R N K I T G T I L F F   Majority
                         400               410               420
347     C C L Y - - P Q V I V D H P F F F L I R N R R T G T I L F M   84476
380     R T G H G G P Q F V A D H P F L F L I M H K I T N C I L F F   PAI-2

G R V M H P E T M N T S G H D F S S L                         Majority
                         430
375     G R V M H P E T M N T S G H D F E E L                         84476
410     G R - - - - - - - - - - - - - F S S P                         PAI-2
```

FIGURE 2D

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1558 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: Hypothalamus
      (B) CLONE: 84476

(xi) SEQUENCE DESCRIPTION: SEQ ID NO:1:

```
AATTCGGCAC GAGGGAAAGG AGAGGAAGGG GGGGGCAAGC CCTCACCTGC GCCAATCAGG      60

GTTTGAAACT GTTACAATAT GGCTTTCCTG GGACTCTTCT CTTTGCTGGT TCTGCAGAGT     120

ATGGCTACAG GGGCCACTTT CCCTGAGGAA GCCATTGTTG ACTTGTCAGT GAATATGTAT     180

AATCGTCTTA GAGCCACTGG TGAAGATGAA AATATTCTCT TCTCTCCATT GAGTATTGCT     240

CTTGCAATGG GAATGATGGA ACTTGGGGCC CAAGGATCTA CCCAGAAAGA AATCCGCCAC     300
```

-continued

```
TCAATGGGAT ATGACAGCCT AAAAAATGGT GAAGAATTTT CTTTCTTGAA GGAGTTTTCA      360

AACATGGTAA CTGCTAAAGA GAGCCAATAT GTGATGAAAA TTGCCAATTC CTTGTTTGTG      420

CAAAATGGAT TTCATGTCAA TGAGGAGTTT TTGCAAATGA TGAAAAAATA TTTTAATGCA      480

GCAGTAAATC ATGTGGACTT CAGTCAAAAT GTAGCCGTGG CCAACTACAT CAATAAGTGG      540

GTGGAGAATA ACACAAACAA TCTGGTGAAA GATTTGGTAT CCCCAAGGGA TTTTNATGCT      600

GCCACTTATC TGGCCCTCAT TAATGCTGTC TATTTCAAGG GGAACTGGAA GTCGCAGTTT      660

AGGCCTGAAA ATACTAGAAC CTTTTCTTTC ACTAAAGATG ATGAAAGTGA AGTCCAAATT      720

CCAATGATGT ATCAGCAAGG AGAATTTTAT TATGGGGAAT TTAGTGATGG CTCCAATGAA      780

GCTGGTGGTA TCTACCAAGT CCTAGAAATA CCATATGAAG GAGATGAAAT AAGCATGATG      840

CTGGTGCTGT CCAGACAGGA AGTTCCTCTT GCTACTCTGG AGCCATTAGT CAAAGCACAG      900

CTGGTTGAAG AATGGGCAAA CTCTGTGAAG AAGCAAAAAG TAGAAGTATA CCTGCCCAGG      960

TTCACAGTGG AACAGGAAAT TGATTTAAAA GATGTTTTGA AGGCTCTTGG AATAACTGAA     1020

ATTTTCATCA AGATCAAATT TGACAGCCTC TCTGATAATA AGGAGATTTT TCTTTCCAAA     1080

GCAATTCACA AGTCCTTCCT AGAGGTTAAT GAAGAAGGCT CAGAACTCTC TGTCTCAGGA     1140

ATGATTCAAT TAGTAGGATG CTGTCTGTAT CCTCAAGTTA TTGTCGACCA TCCATTTTTC     1200

TTTCTTATCA GAAACAGGAG AACTGGTACA ATTCTATTCA TGGGACGAGT CATGCATCCT     1260

GAAACAATGA ACACAAGTGG ACATGATTTC GAAGAACTTT AAGTTACTTT ATTTGAATAA     1320

CAAGGAAAAC AGTAACTAAG CACATTATGT TTGCAACTGG TATATATTTA GGATTTGTGT     1380

TTTACAGTAT ATCTTAAGAT AATATTTAAA ATAGTTCCAG ATAAAAACAA TATATGTAAA     1440

TTATAAGTAA CTTGTCAAGG AATGTTATCA GTATTAAGCT AATGGTCCTG TTATGTCATT     1500

GTGTTTGTGT GCTGTTGTTT AAAATAAAAG TACCTATTGA AAAAAAAAAA AAAAAAA       1558
```

(2) INFORMATION FOR SEQ ID NO:2:

(i) SEQUENCE CHARACTERISTICS:
        (A) LENGTH: 407 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Phe Leu Gly Leu Phe Ser Leu Leu Val Leu Gln Ser Met Ala
 1               5                  10                  15

Thr Gly Ala Thr Phe Pro Glu Glu Ala Ile Val Asp Leu Ser Val Asn
             20                  25                  30

Met Tyr Asn Arg Leu Arg Ala Thr Gly Glu Asp Glu Asn Ile Leu Phe
         35                  40                  45

Ser Pro Leu Ser Ile Ala Leu Ala Met Gly Met Glu Leu Gly Ala
     50                  55                  60

Gln Gly Ser Thr Gln Lys Glu Ile Arg His Ser Met Gly Tyr Asp Ser
65                  70                  75                  80

Leu Lys Asn Gly Glu Glu Phe Ser Phe Leu Lys Glu Phe Ser Asn Met
                 85                  90                  95

Val Thr Ala Lys Glu Ser Gln Tyr Val Met Lys Ile Ala Asn Ser Leu
            100                 105                 110

Phe Val Gln Asn Gly Phe His Val Asn Glu Glu Phe Leu Gln Met Met
        115                 120                 125

Lys Lys Tyr Phe Asn Ala Ala Val Asn His Val Asp Phe Ser Gln Asn
```

```
              130                 135                 140
Val Ala Val Ala Asn Tyr Ile Asn Lys Trp Val Glu Asn Asn Thr Asn
145                 150                 155                 160

Asn Leu Val Lys Asp Leu Val Ser Pro Arg Asp Phe Xaa Ala Ala Thr
                165                 170                 175

Tyr Leu Ala Leu Ile Asn Ala Val Tyr Phe Lys Gly Asn Trp Lys Ser
                180                 185                 190

Gln Phe Arg Pro Glu Asn Thr Arg Thr Phe Ser Phe Thr Lys Asp Asp
                195                 200                 205

Glu Ser Glu Val Gln Ile Pro Met Met Tyr Gln Gln Gly Glu Phe Tyr
    210                 215                 220

Tyr Gly Glu Phe Ser Asp Gly Ser Asn Glu Ala Gly Gly Ile Tyr Gln
225                 230                 235                 240

Val Leu Glu Ile Pro Tyr Glu Gly Asp Glu Ile Ser Met Met Leu Val
                245                 250                 255

Leu Ser Arg Gln Glu Val Pro Leu Ala Thr Leu Glu Pro Leu Val Lys
                260                 265                 270

Ala Gln Leu Val Glu Glu Trp Ala Asn Ser Val Lys Lys Gln Lys Val
                275                 280                 285

Glu Val Tyr Leu Pro Arg Phe Thr Val Glu Gln Glu Ile Asp Leu Lys
    290                 295                 300

Asp Val Leu Lys Ala Leu Gly Ile Thr Glu Ile Phe Ile Lys Ile Lys
305                 310                 315                 320

Phe Asp Ser Leu Ser Asp Asn Lys Glu Ile Phe Leu Ser Lys Ala Ile
                325                 330                 335

His Lys Ser Phe Leu Glu Val Asn Glu Glu Gly Ser Glu Leu Ser Val
                340                 345                 350

Ser Gly Met Ile Gln Leu Val Gly Cys Cys Leu Tyr Pro Gln Val Ile
                355                 360                 365

Val Asp His Pro Phe Phe Phe Leu Ile Arg Asn Arg Arg Thr Gly Thr
    370                 375                 380

Ile Leu Phe Met Gly Arg Val Met His Pro Glu Thr Met Asn Thr Ser
385                 390                 395                 400

Gly His Asp Phe Glu Glu Leu
                405

(2) INFORMATION FOR SEQ ID NO:3:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:3:

Met Glu Asp Leu Cys Val Ala Asn Thr Leu Phe Ala Leu Asn Leu Phe
1               5                   10                  15

Lys His Leu Ala Lys Ala Ser Pro Thr Gln Asn Leu Phe Leu Ser Pro
            20                  25                  30
```

```
Trp Ser Ile Ser Ser Thr Met Ala Met Val Tyr Met Gly Ser Arg Gly
     35                  40                  45

Ser Thr Glu Asp Gln Met Ala Lys Val Leu Gln Phe Asn Glu Val Gly
 50                  55                  60

Ala Ala Ala Asp Lys Ile His Ser Ser Phe Arg Ser Leu Ser Ser Ala
 65                  70                  75                  80

Ile Asn Ala Ser Thr Gly Asn Tyr Leu Leu Glu Ser Val Asn Lys Leu
                 85                  90                  95

Phe Gly Glu Lys Ser Ala Ser Phe Arg Glu Glu Tyr Ile Arg Leu Cys
             100                 105                 110

Gln Lys Tyr Tyr Ser Ser Glu Pro Gln Ala Val Asp Phe Leu Glu Cys
         115                 120                 125

Ala Glu Glu Ala Arg Lys Lys Ile Asn Ser Trp Val Lys Thr Gln Thr
 130                 135                 140

Lys Gly Lys Ile Pro Asn Leu Leu Pro Glu Gly Ser Val Asp Gly Asp
145                 150                 155                 160

Thr Arg Met Val Leu Val Asn Ala Val Tyr Phe Lys Gly Lys Trp Lys
                165                 170                 175

Thr Pro Phe Glu Lys Lys Leu Asn Gly Leu Tyr Pro Phe Arg Val Asn
            180                 185                 190

Ser Ala Gln Arg Thr Pro Val Gln Met Met Tyr Leu Arg Glu Lys Leu
        195                 200                 205

Asn Ile Gly Tyr Ile Glu Asp Leu Lys Ala Gln Ile Leu Glu Leu Pro
210                 215                 220

Tyr Ala Gly Asp Val Ser Met Phe Leu Leu Leu Pro Asp Glu Ile Ala
225                 230                 235                 240

Asp Val Ser Thr Gly Leu Glu Leu Leu Glu Ser Glu Ile Thr Tyr Asp
                245                 250                 255

Lys Leu Asn Lys Trp Thr Ser Lys Asp Lys Met Ala Glu Asp Glu Val
            260                 265                 270

Glu Val Tyr Ile Pro Gln Phe Lys Leu Glu Glu His Tyr Glu Leu Arg
        275                 280                 285

Ser Ile Leu Arg Ser Met Gly Met Glu Asp Ala Phe Asn Lys Gly Arg
290                 295                 300

Ala Asn Phe Ser Gly Met Ser Glu Arg Asn Asp Leu Phe Leu Ser Glu
305                 310                 315                 320

Val Phe His Gln Ala Met Val Asp Val Asn Glu Glu Gly Thr Glu Ala
                325                 330                 335

Ala Ala Gly Thr Gly Gly Val Met Thr Gly Arg Thr Gly His Gly Gly
            340                 345                 350

Pro Gln Phe Val Ala Asp His Pro Phe Leu Phe Leu Ile Met His Lys
        355                 360                 365

Ile Thr Asn Cys Ile Leu Phe Phe Gly Arg Phe Ser Ser Pro
370                 375                 380

(2) INFORMATION FOR SEQ ID NO:4:

(i) SEQUENCE CHARACTERISTICS:
        (A) LENGTH: 420 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

(v) FRAGMENT TYPE: N-terminal (vi) ORIGINAL SOURCE:

(xi) SEQUENCE DESCRIPTION: SEQ ID NO:4:

```
Met Ala Phe Leu Gly Leu Phe Ser Leu Leu Val Leu Glu Ser Leu Ala
 1               5                  10                  15

Val Gly Ala Thr Leu Pro Glu Glu Ala Ile Val Asp Leu Ala Val Asn
            20                  25                  30

Leu Phe Asn His Leu Ala Ala Ala Gly Glu Thr Glu Asn Leu Leu Leu
        35                  40                  45

Ser Pro Leu Ser Ile Ala Leu Ala Met Gly Met Val Glu Leu Gly Ala
    50                  55                  60

Gln Gly Ser Thr Glu Asp Glu Ile Ala Lys Val Leu Gly Phe Asp Ser
65                  70                  75                  80

Val Gly Ala Gly Ala Asp Lys Ile His Ser Ser Leu Lys Ser Leu Ser
                85                  90                  95

Ser Ala Val Thr Ala Ser Thr Gly Asn Tyr Val Leu Glu Ile Ala Asn
            100                 105                 110

Ser Leu Phe Gly Glu Asn Gly Ala Ser Val Asn Glu Glu Phe Leu Gln
        115                 120                 125

Leu Cys Gln Lys Tyr Phe Ser Ala Ala Val Asn Ala Val Asp Phe Leu
    130                 135                 140

Glu Asn Ala Ala Val Ala Arg Asn Lys Ile Asn Ser Trp Val Glu Thr
145                 150                 155                 160

Asn Thr Asn Gly Leu Val Lys Asp Leu Val Ser Glu Gly Ser Val Xaa
                165                 170                 175

Gly Ala Thr Arg Leu Ala Leu Val Asn Ala Val Tyr Phe Lys Gly Asn
            180                 185                 190

Trp Lys Ser Gln Phe Glu Lys Glu Leu Thr Gly Leu Phe Ser Phe Thr
        195                 200                 205

Val Asp Ser Ala Ser Glu Val Gln Val Gln Met Met Tyr Leu Gln Gly
    210                 215                 220

Glu Leu Asn Ile Gly Glu Phe Ile Asp Gly Leu Asn Ala Ala Gly Gly
225                 230                 235                 240

Ile Tyr Gln Val Leu Glu Leu Pro Tyr Ala Gly Asp Glu Val Ser Met
                245                 250                 255

Phe Leu Val Leu Ser Asp Glu Ile Ala Asp Val Ala Thr Gly Leu Glu
            260                 265                 270

Leu Leu Glu Ser Leu Val Thr Ala Asp Leu Val Glu Glu Trp Ala Ser
        275                 280                 285

Ser Val Lys Lys Ala Glu Asp Glu Val Glu Val Tyr Leu Pro Gln Phe
    290                 295                 300

Thr Val Glu Glu Glu Ile Asp Leu Lys Ser Val Leu Lys Ala Leu Gly
305                 310                 315                 320

Ile Thr Asp Ala Phe Ile Lys Gly Lys Ala Asn Phe Ser Gly Leu Ser
                325                 330                 335

Asp Asn Asn Asp Leu Phe Leu Ser Glu Ala Ile His Gln Ala Phe Val
            340                 345                 350

Asp Val Asn Glu Glu Gly Ser Glu Ala Ala Gly Gly Gly Gly Val
        355                 360                 365

Leu Val Gly Arg Thr Gly His Gly Pro Gln Val Val Ala Asp His
    370                 375                 380

Pro Phe Leu Phe Leu Ile Arg Asn Lys Ile Thr Gly Thr Ile Leu Phe
```

```
385                390                395                400
Phe Gly Arg Val Met His Pro Glu Thr Met Asn Thr Ser Gly His Asp
                405                410                415
Phe Ser Ser Leu
            420
```

(2) INFORMATION FOR SEQ ID NO:5:

(i) SEQUENCE CHARACTERISTICS:
        (A) LENGTH: 406 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:5:

```
Met Ala Thr Gly Ala Val Phe Pro Glu Glu Ala Ile Val Leu Leu Ala
 1               5                  10                 15
Val Asn Leu Phe Asn His Leu Ala Ala Ala Gly Glu Thr Glu Asn Leu
                20                  25                 30
Leu Leu Ser Pro Leu Ser Ile Ala Leu Ala Met Gly Met Val Glu Leu
                35                  40                 45
Gly Ala Gln Gly Ser Thr Glu Asp Glu Ile Ala Lys Val Leu Gly Phe
        50                  55                  60
Asp Ser Val Gly Ala Gly Ala Asp Lys Ile His Ser Ser Leu Lys Ser
65                  70                  75                 80
Leu Ser Ser Ala Val Thr Ala Ser Thr Gly Asn Tyr Val Leu Glu Ile
                85                  90                 95
Ala Asn Ser Leu Phe Gly Glu Asn Gly Ala Ser Val Asn Glu Glu Phe
                100                 105                110
Leu Gln Leu Cys Gln Lys Tyr Phe Ser Ala Ala Val Asn Ala Val Asp
            115                 120                 125
Phe Leu Glu Asn Ala Ala Val Ala Arg Asn Lys Ile Asn Ser Trp Val
        130                 135                 140
Glu Thr Asn Thr Asn Gly Leu Val Lys Asp Leu Val Ser Gly Ser Ser
145                 150                 155                160
Val Xaa Gly Ala Thr Arg Leu Ala Leu Val Asn Ala Val Tyr Phe Lys
                165                 170                175
Gly Asn Trp Lys Ser Gln Phe Glu Lys Glu Leu Thr Gly Leu Phe Ser
            180                 185                 190
Phe Thr Val Asp Ser Ala Ser Glu Val Gln Val Gln Met Met Tyr Leu
        195                 200                 205
Gln Gly Glu Leu Asn Ile Gly Glu Phe Ile Asp Gly Leu Asn Ala Ala
        210                 215                 220
Gly Gly Ile Tyr Gln Val Leu Glu Leu Pro Tyr Ala Gly Asp Glu Val
225                 230                 235                240
Ser Met Phe Leu Val Leu Ser Asp Glu Ile Ala Asp Val Ala Thr Gly
                245                 250                255
Leu Glu Leu Leu Glu Ser Leu Val Thr Ala Asp Leu Val Glu Glu Trp
                260                 265                270
```

-continued

```
Ala Ser Ser Val Lys Lys Ala Glu Asp Glu Val Glu Val Tyr Leu Pro
        275                 280                 285

Gln Phe Thr Val Glu Glu Glu Ile Asp Leu Lys Ser Val Leu Lys Ala
        290             295                 300

Leu Gly Ile Thr Asp Ala Phe Ile Lys Gly Lys Ala Asn Phe Ser Gly
305                 310                 315                 320

Leu Ser Asp Asn Asn Asp Leu Phe Leu Ser Glu Ala Ile His Gln Ala
            325                 330                 335

Phe Val Asp Val Asn Glu Glu Gly Ser Glu Ala Ala Ala Gly Gly Gly
            340                 345                 350

Gly Val Leu Val Gly Arg Thr Gly His Gly Gly Pro Gln Val Val Ala
        355                 360                 365

Asp His Pro Phe Leu Phe Leu Ile Arg Asn Lys Ile Thr Gly Thr Ile
    370                 375                 380

Leu Phe Phe Gly Arg Val Met His Pro Glu Thr Met Asn Thr Ser Gly
385                 390                 395                 400

His Asp Phe Ser Ser Leu
            405
```

ASSAY METHOD TO DETECT SERPIN DERIVED FROM HUMAN HYPOTHALAMUS

This application is a divisional application of U.S. application Ser. No. 08/997,040, filed Dec. 23, 1997 which is a divisional of U.S. application Ser. No. 08/487,823, filed Jun. 7, 1995, now U.S. Pat. No. 5,700,924.

FIELD OF THE INVENTION

The present invention is in the field of molecular biology; more particularly, the present invention describes the nucleic acid and amino acid sequences of a novel serpin expressed in the hypothalamus.

BACKGROUND OF THE INVENTION

Inhibitory Serpins

Serpins are irreversible serine protease inhibitors which are principally located extracellularly. As a group, they are defined on the basis of their structural and functional characteristics: a high molecular weight (between 370–420 amino acid residues), and a C-terminal reactive region. Proteins which have been assigned to the serpin family include the following: α-1 protease inhibitor, α-1-antichymotrypsin, antithrombin III, α-2-antiplasmin, heparin cofactor II, complement C1 inhibitor, plasminogen activator inhibitors 1 and 2, glia derived nexin, protein C inhibitor, rat hepatocyte inhibitors, crmA (a viral serpin which inhibits interleukin 1-β cleavage enzyme), human squamous cell carcinoma antigen which may modulate the host immune response against tumor cells, human maspin which seems to function as a tumor suppressor, lepidopteran protease inhibitor, leukocyte elastase inhibitor (the only known intracellular serpin), and products from three orthopoxviruses (these products may be involved in the regulation of the blood clotting cascade and/or of the complement cascade in the mammalian host).

Serpins form tight complexes with their target proteases. The serpin region which binds to the target protease is a mobile, exposed reactive site loop (RSL) which contains the P1—P1' bond that is cleaved. When the characteristic serpin P1—P1' bond cleaves, the serpin structure changes profoundly, and stability to heat- or guanidine-induced denaturation increases markedly. These changes are referred to as the stressed-to-relaxed (S→R) transition, and are associated with tight complex formation with specific proteases. For the α1-proteinase inhibitor, cleavage of the P1—P1' bond results in a separation of about 69 Å between the two residues (Loebermann H et al (1984) J Mol Biol 177:531–556). The ability of a serpin to function as an inhibitor may be directly related to its ability to undergo this S→R transition (Bruch M et al (1988) J Biol Chem 263: 16626–30; Carrell RW et al (1992) Curr Opin Struct Biol 2:438–446).

In addition, the RSL sequence from P17 to P8 (hinge region) is highly conserved, and small amino acid with side chains are found at positions P9, P10, P11, P12, and P15 in active inhibitors. The presence of small amino acids in this region allows the peptide loop from P14–P2 to be inserted into the middle of the protease inhibitor A-sheet. The insertion of this sequence into the A-sheet appears to be important in stabilizing the inhibitor, and consequently tightening the protease/serpin complex. Sequence divergence in the hinge region may convert an inhibitor to a substrate.

Noninhibitory Serpins

A number of proteins with no known inhibitory activity are also categorized as serpins on the basis of strong sequence and structural similarities. These proteins can be cleaved by specific proteases, but do not form the tight complexes that inhibit protease activity. Examples are bird ovalbumin, angiotensinogen, barley protein Z, corticosteroid binding globulin, thyroxine binding globulin, sheep uterine milk protein, pig uteroferrin-associated protein, an endoplasmic reticulum heat-shock protein (which binds strongly to collagen and could act as a chaperone), pigment epithelium-derived factor, and an estrogen-regulated protein from Xenopus.

The nature of the difference between inhibitory and noninhibitory serpins is not well understood. For example, ovalbumin is unable to undergo this S→R transition (Mottonen et al (1992) Nature 355: 270–273). However, hormone binding globulins, such as thyroxine or cortisol binding globulins, apparently do undergo the transition from the native stressed to relaxed conformation upon protease cleavage but do not form a tight complex with specific proteases (Pemberton et al (1988) Nature 336: 257–258). The S→R transition may confer an advantage for hormone binding molecules, and for small molecule binding proteins in general, in that the transition from a stressed to a relaxed conformation may provide a method for modulating hormone delivery. Both hormone binding globulins have a greater than 30% homology with the archetype of the serpin family, alpha-1-antitrypsin, and sequence matching infers that they all share a common secondary and tertiary structure.

Serpins are defined and described in Carrell R and Travis J (1985) Trends Biochem Sci 10:20–24; Carrell R et al (1987) Cold Spring Harbor Symp Quant Biol 52:527–535; Huber R and Carrell R W (1989) Biochemistry 28:8951–8966; and Remold-O'Donneel E (1993) FEBS Lett 315:105–108.

The novel serpin which is the subject of this application was identified among the cDNAs of a pooled hypothalamus library.

The Hypothalamus

The hypothalamus, the master gland of the human body, is an area of neuroendocrine cells on the floor and midline of the human brain. It is intimately associated with the nervous system function. The anterior hypothalamus mostly interacts with parasympathetic pathways, and the posterior with sympathetic. Functionally, the hypothalamus is divided into chiasmatic, tuberal and mammillary regions.

The chiasmatic region which develops prenatally has three prominent components, the supraoptic, paraventricular and accessory neurosecretory nuclei; the sexually dimorphic intermediate nucleus (SDN); and the suprachiasmatic nucleus (SCN). The large supraoptic (SON) and paraventricular neurons (PVN) of the chiasmatic region are unmyelinated and produce antidiuretic hormone (ADH) and oxytocin; the enzyme, tyrosine hydroxylase; and the monoamine neurotransmitter, dopamine. Subsequently, ADH and oxytocin are stored in the anterior pituitary gland. PVN neurons also produce somatostatin. The neurosecretory granules of these large-celled neurons produce small amounts of dynorphin, enkephalins, galanin, cholecystokinin, and neuropeptide Y which appear to function as local paracrine agents.

The small accessory neurosecretory neurons produce ADH, tyrosine hydroxylase, neuropeptide Y, and corticotropin releasing hormone (CRH) and have prominent dopamine synapses. Neurons of the chiasmatic region contain gamma amino butyric acid (GABA), glutamate, quisqualate, relaxin, melatonin, angiotensin-1, endothelin, N-methyl-D-aspartate (NMDA), neurophysin, and β-adrenergic receptors (Morris JF and Pow DV (1993) Ann NY Acad Sci 689:16–33; Renaud LP et al (1992) Prog Brain Res 92:277–288). Projections of all three types of chiasmatic neurons communicate with many regions of the central nervous system including the brain stem, limbic system, retina and spinal cord.

The sexually dimorphic nucleus (SDN), also known as the intermediate nucleus, is located between the supraoptic and paraventricular nuclei. The SDN appears to be sensitive to steroidal hormones and develops twice as many cells and is twice as large in males (0.2 mm$^3$) as in females (0.1 mm$^3$) after the age of four. The number of cells decreases with senescence (at 50 years of age for men and 70, for women); however, cause and effect of associated hormones have not been established.

The superchiasmatic nucleus (SCN) is considered to be the circadian pacemaker of the mammalian brain coordinating both hormonal and behavioral rhythms. The SCN is sexually dimorphic, elongated in women and spherical in men; and the number and volume of SCN cells varies with age and season. Biochemical and immunological studies indicate that serotonin and melanin in concert with G-protein associated/cyclic adenosine monophosphate-linked receptors regulate circadian rhythms (Erlander MG et al (1993) J Biol Rhythms 8S:25–31).

The retinohypothalamic tract is a monosynaptic pathway that links the retina to the SCN and helps set the intrinsic period, phase, and amplitude of the internal biological clock. Total blindness which prevents light/dark synchronization results in free-running rhythms, particularly in cortisol, melatonin, sleep, and temperature regulation. A lesion or tumor in the area of the SCN can also be correlated with disturbed circadian rhythms.

The hypothalamic neurons of the tuberal and mammillary regions produce a variety of regulatory peptides called releasing hormones or factors which modulate much of human endocrine function. These short oligopeptide releasing factors are secreted and delivered to the anterior pituitary via the fenestrated capillary network of the hypothalamic pituitary portal system. Each region will be discussed in turn.

The tuberal region is composed of a complex of ventromedial (VMN), dorsomedial (DMN), lateral tuberal (NTL), and infundibular nuclei (Braak, H and Braak, E (1992) Prog Brain Res 93:3–14). These nuclei function in feeding, aggressive and sexual behaviors, and they secrete growth hormone releasing hormone (GRH), thyroid releasing hormone (TRH) and luteinizing hormone releasing hormone (LHRH). The networked VMN has projections to the basal forebrain as well as to all parts of the cerebral cortex where it is assumed to influence higher cortical function.

The DMN is poorly differentiated in the human brain and covers the anterior and superior areas of the VMN. Its neurons contain catecholamine, somatostatin, neuropeptide Y and neurotensin, neurokinin B (NKB), and LHRH. The NKB neurons may participate negative feedback of estrogen on LHRH and act as an intemeuron on LHRH nuclei.

The NTL is only present in higher primates. The NTL is characterized by cholinergic, CRH, somatostatin, benzodiazepin and NMDA receptors. Neuronal loss in this region may predict disease severity, particularly in Kallmann's and Down's syndromes and in Alzheimer's and Huntington's diseases.

The exact role of the mammillary nucleus is poorly defined. Most of its neurons project into the cortex and are responsible for the major histaminergic innervation. Some evidence indicates the mammillary region is involved in heat regulation and governs capillary restriction, sweating, shivering and piloerection.

Nonendocrine functions of the hypothalamus include regulation of food intake and feeding behavior, temperature regulation, sleep-wake cycle, memory, behavior, and thirst. Although the basal hypothalamus is known to control stable weight, both the VMN and the anterior hypothalamus are involved in regulation of hunger and satiety. Appetite is stimulated by GABA, dopamine, beta-endorphins, enkephalin and neuropeptide Y and inhibited by serotonin, norepinephrine, cholecystokinin, neurotensin, TRH, naloxone, somatostatin, and vasoactive intestinal peptide. A lesion or tumor in the area of the VMN can cause hypothalamic obesity. Other factors, particularly the thyroid and adrenal hormones, also affect eating behavior.

The anterior hypothalamus contains neurons that respond to local and environmental thermal gradients. Heat production is stimulated by serotonin and blocked by norepinephrine and epinephrine. When infections occur, phagocytic cells produce interleukin-1 (IL-1). IL-1 stimulates the anterior hypothalamus to produce prostaglandin E2 which increases the body temperature set point and produces fever. Cooling or heat dissipation which involves vasodilation is governed by the posterior hypothalamus. Hypothalamic disease (with or without malfunction of the thyroid or adrenal glands) may cause hypothermia, hyperthermia or poikilothermia.

The sleep center is located in the anterior hypothalamus where disturbances or lesions can lead to insomnia or agitation. The posterior hypothalamus is responsible for arousal and maintenance of the waking state. Serotonin promotes sleep, while catecholamines aid wakefulness. Destruction of the posterior hypothalamus, for example, by ischemia and encephalitis, trauma or tumor can result in hypersomnolence.

Thirst is controlled by serum osmolality and is detected by osmoregulators in the hypothalamus. Nerve impulses control the pituitary release of vasopressin which acts upon the kidney. In the case of pathological disturbances, interactions among the nervous system, endocrine hormones, and cytokines (particularly IL-1) modulate the activity of these glands and the kidney. Impaired thirst is commonly attributable to hypothalamic lesions.

The effects of ACTH, ADH, and oxytocin memory and behavior are still being investigated. Lesions of the ventromedial hypothalamus produce rage while ventromedial, dorsomedial and/or mammillary lesions cause loss of short term memory. Lateral hypothalamic destruction can cause apathetic behavior, but large hypothalamic lesions are associated with dementia.

Diseases Associated with the Hypothalamus

Many diseases are associated with changes in hypothalamic function and structure.

The most common hypothalamic disease is hyperprolactinemia, excess prolactin production, which may lead to galactorrhea and/or hypogonadism. Another disease is dwarfism, likely caused by the overproduction of somatostatin which prevents growth hormone release. Tumors are the most common cause of the over- or under-production of hypothalamic hormones. Cushing's disease is caused by tumors overproducing ACTH. Finally, the hypothalamus or the molecules it produces may also be responsible for some of the symptoms in neurodegenerative diseases such as Alzheimer's, Parkinson's, and Huntington's diseases.

Hypothalamic anatomy, physiology, and diseases are reviewed, inter alia, in Guyton AC (1991) Textbook of Medical Physiology, WB Saunders Co, Philadelphia Pa.;

Isselbacher KJ et al (1994) Harrison's Principles of Internal Medicine, McGraw Hill, New York City; The Merck Manual of Diagnosis and Therapy (1992) Merck Research Laboratories, Rahway N.J.; and Swaab DB et al (1993) Anat Embryol 187:317–330.

Some of these diseases may be difficult to diagnose or treat. Modem techniques for diagnosis of abnormalities in the hypothalamus mainly rely on observation of clinical symptoms, serological analysis of hormone levels, or measurement of urinary excretion of a hormone or its metabolites. Alternatively, computerized axial tomography (CAT scan) or Magnetic Resonance Imaging (MRI) can be used to observe abnormal histological changes of the hypothalamic region. Thus, development of new techniques becomes necessary for early and accurate diagnosis or for treatments of diseases associated with the hypothalamus.

SUMMARY OF THE INVENTION

The subject invention provides a unique nucleotide sequence (cape) which encodes a novel serpin (CAPE). The nucleotide sequence, which was identified from Incyte Clone 84476 derived from hypothalamic cells, contains two ATG codons downstream from the last stop codon of the previous gene. The two ATGs predict the expression of two different proteins: CAPE1 and CAPE2. However only CAPE1 includes a good signal sequence.

The subject invention includes the antisense DNA of cape; cloning or expression vectors containing cape; host cells or organisms transformed with expression vectors containing cape; a method for the production and recovery of purified CAPE polypeptide from host cells; purified CAPE polypeptide; antibodies to both polypeptides; and pharmacological compounds using CAPE for the treatment of disease.

Furthermore, the subject invention also comprises diagnostic tests for pathologically compromised brain tissues including but not limited to the hypothalamus which include the steps of testing a sample or an extract thereof with cape DNA, fragments or oligomers thereof.

DESCRIPTION OF THE FIGURES.

FIGS. 1A and 1B show the nucleotide sequence for cape including the entire coding sequence and the predicted amino acid sequences for CAPE1 and CAPE2 polypeptides. The start codon for CAPE1 is at nucleotide 79; whereas the start codon for CAPE2 is at nucleotide 121.

FIGS. 2A, 2B, 2C, and 2D display the alignment of CAPE1 and CAPE2, respectively, with plasminogen activator inhibitor 2 (PAI-2). The majority sequence is a consensus sequence. Alignments shown were produced using the multisequence alignment program of DNASTAR software (DNASTAR Inc, Madison Wis.).

DETAILED DESCRIPTION OF THE INVENTION

Definitions

Figure 3:
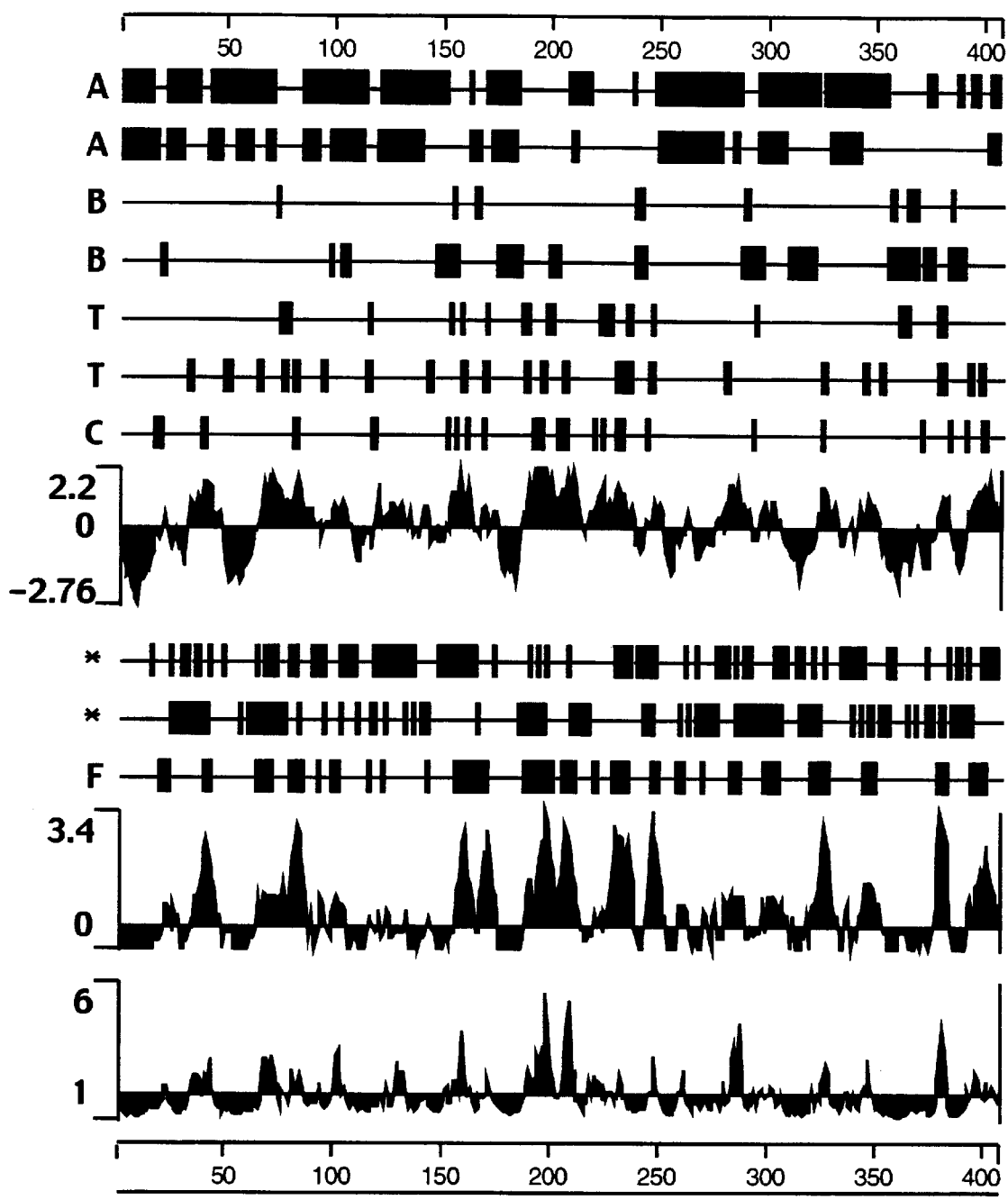
FIG. 3 provides structural analysis of the cape sequence for determining putative alpha (A), beta (B), turn (T), and coil (C) regions; a hydrophilicity plot (H); alpha and beta amphipathic regions (*); flexible regions (F); a putative antigenic index (AI); and a surface probability plot (S) using the structural analysis program of DNASTAR software (DNASTAR Inc, Madison Wis.).

As used herein, CAPE1 and CAPE2 refer to novel serpins, naturally occurring, or active fragments thereof, which are encoded by mRNAs transcribed from the cDNA (cape) of Seq ID NO 1. The amino acid sequence of CAPE 1 is shown in SEQ ID NO 2 starting at residue 27 and terminating at residue 519, and that of CAPE2 is shown in SEO ID NO 2 starting at residue 41 and terminating at residue 519. The abbreviation CAPE will be used to describe CAPE1 and CAPE2 generally.

"Active" refers to those forms of CAPE which retain biologic and/or immunologic activities of any naturally occurring CAPE.

"Naturally occurring CAPE" refers to CAPE produced by human cells that have not been genetically engineered and specifically contemplates various forms arising from post-translational modifications of the polypeptide, including but not limited to acetylation, carboxylation, glycosylation, phosphorylation, lipidation and acylation.

"Derivative" refers to polypeptides derived from naturally occurring CAPE by chemical modifications such as ubiquitination, labeling (e.g., with radionuclides, various enzymes, chromogenic or fluorogenic means), pegylation (derivatization with polyethylene glycol), or by insertion (or substitution by chemical synthesis) of amino acids such as ornithine, which do not normally occur in human proteins.

"Recombinant variant" refers to any polypeptide differing from naturally occurring CAPE by amino acid (aa) insertions, deletions, and substitutions, created using recombinant DNA techniques. Guidance in determining which aa residues may be replaced, added or deleted without abolishing activities of interest, such as protein proteolysis, protease inhibition, or small molecule binding properties, may be found by comparing the sequence of the particular CAPE with that of homologous inhibitory and noninhibitory serpins and minimizing the number of aa sequence changes made in regions of high homology.

Preferably, aa "substitutions" are the result of replacing one aa with another aa having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 aa. The variation allowed may be experimentally determined by systematically making insertions, deletions, or substitutions of aa in a CAPE molecule using recombinant DNA techniques and assaying the resulting recombinant variants for activity.

A "signal sequence" can direct a polypeptide to a specific location in a cell or to a specific destination outside of the cell. Such a sequence may be naturally present on the polypeptide of the present invention or provided from heterologous protein sources by recombinant DNA techniques.

A polypeptide "fragment," "portion," or "segment" is a stretch of aa residues of at least about 5 aa, often at least about 7 aa, typically at least about 9 to 13 aa, and, in various embodiments, at least about 17 or more aa. To be active, any CAPE polypeptide must have sufficient length to display biologic and/or immunologic activity on their own or when conjugated to a carrier protein such as keyhole limpet hemocyanin (KLH, Sigma).

"Small molecules" are molecules with a molecular weight under 5000, more preferably under 2000. The small molecules of particular interest may be derived from the hypothalamus, such as oxytocin, vasopressin, dopamine, neuropeptide Y, somatostatin, or enkephalins. These small molecules may directly affect the hypothalamus or other target neuronal tissues, such as the pituitary gland. Alternatively, the small molecules may be derived from other tissues and affect the hypothalamus. These small molecules may include, but are not limited to, molecules such as serotonin, epinephrine, norepinephrine, gamma amino butyric acid, glutamate, or other neurotransmitters or hormones. These small molecules may be naturally occurring or synthetically made.

"Conditions associated with altered expression of CAPE" refer to physiological or pathological changes of the hypothalamus or other neuronal tissues. Pathological changes include inflammation, disease and tumors.

"Hypothalamic tissue" refers to tissue derived mostly from the hypothalamus, but which may include other tissue from organs that surround or are adjacent to the hypothalamus.

"Animal" as used herein may be defined to include human, domestic, or agricultural (cats, dogs, cows, sheep, etc.) or test species (mouse, rat, rabbit, etc.).

An "oligonucleotide" or polynucleotide "fragment", "portion," or "segment" is a stretch of nucleotide residues which is long enough to use in polymerase chain reaction (PCR) or various hybridization procedures. Oligonucleotide probes will comprise sequence that is identical or complementary to a portion of cape where there is little or no identity or complementarity with any known or prior art molecule. The oligonucleotide probes will generally comprise between about 10 nucleotides and 50 nucleotides, and preferably between about 15 nucleotides and about 30 nucleotides. Nucleic acid probes comprise portions of the cape sequence having fewer nucleotides than about 6 kb, preferably fewer than about 1 kb. After appropriate testing to eliminate false positives, both oligonucleotide and nucleic acid probes may be used to determine whether mRNAs encoding CAPE are present in a cell or tissue or to isolate similar natural nucleic acid sequences from chromosomal DNA as described by Walsh, et al (1992) PCR Methods Appl 1:241–50.

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labelling are elaborated in Sambrook, et al (1989) Molecular Cloning: A Laboratory Manual, Cold Spring Harbor N.Y., or Ausubel, et al (1989) Current Protocols in Molecular Biology, John Wiley & Sons, New York City, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, including but not limited to small molecule-binding affinities, or polypeptide degradation or turnover rate.

The present invention includes purified CAPE polypeptide from natural or recombinant sources, and cells transformed with recombinant nucleic acid molecules encoding CAPE. Various methods for the isolation of the polypeptide may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology, Vol 182, Academic Press, San Diego Calif.; and Scopes R (1982) Protein Purification: Principles and Practice. Springer-Verlag, New York City, both incorporated herein by reference.

DETAILED DESCRIPTION OF THE INVENTION

The present invention provides a nucleotide sequence (cape) for a novel serpin, identified in hypothalamic cells. The sequence is provided in SEQ ID NO 1. FIGS. 1A–1C provide the cape nucleotide sequence, and the polypeptide sequence it encodes. Interestingly, the nucleotide sequence contains two alternative start sites (ATG codons) downstream from the stop codon of the previous gene. These start sites serve to express two novel serpins which possess substantial overlap (>95%) in the polypeptide sequence. One encoded protein (CAPE1) is expressed from an ATG codon at nucleotide position 81; its sequence is presented in SEQ ID NO 2 starting at residue 27. The second protein (CAPE2) is expressed from an ATG codon at nucleotide position 121; its sequence is presented in SEQ ID NO 2 starting at residue 41.

FIGS. 2A–2D provide an alignment of CAPE1 and CAPE2, respectively, with plasminogen activation inhibitor-2 (PAI-2), an exemplary serpin family member. CAPE1 contains a good signal sequence consisting of hydrophobic residues indicating that it may be selectively transported from hypothalamic cells to another location such as the pituitary gland. On the other hand, CAPE2, like other serpins, may be secreted from hypothalamic cells. Overall, about 110 out of 406 residues of CAPE2 match exactly with those of PAI-2 (about 27% homology). For the reactive site loop (RSL) residues P10, and P12–16 match exactly, whereas P8, P11, and P17 are substituted by amino acids that are larger by either an extra carbon group, i.e. the presence of threonine versus serine at P11, or a hydroxyl group, i.e. the presence of serine versus alanine at P8.

Since CAPE appears to have an RSL that resembles that of inhibitory serpins, CAPE may inhibit unidentified proteases within or outside of cells. Alternatively, CAPE may serve to bind specific small molecules to maintain higher levels of these molecules inside or outside of a cell and to modulate their release. In fact, the name CAPE was selected because the novel serpin of the subject invention may function either to mask protease activity or to sequester small molecules.

In view of the fact that the cape nucleotide sequence has been identified in hypothalamic cells, the nucleic acid (cape), polypeptide (CAPE), and antibody to CAPE may be useful in investigations of and the intervention in the normal and abnormal function of the numerous endocrine and nonendocrine functions of the hypothalamus. However, even though the cape sequence was found to be expressed in hypothalamic cells it should not be ruled out that cape may be expressed in other cells, particularly other neuronal or secretory cells.

The nucleotide sequence encoding cape has numerous applications in techniques known to those skilled in the art of molecular biology. These techniques include use as hybridization probes, use in the construction of oligomers for PCR, use for chromosome and gene mapping, use in the recombinant production of CAPE and use in the generation of anti-sense DNA or RNA, their chemical analogs and the like. Uses of nucleotides encoding the proteins disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, eg, the triplet genetic code, specific base pair interactions, etc.

It will be appreciated by those skilled in the art that as a result of the degeneracy of the genetic code, a multitude of CAPE-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring CAPE, and all such variations are to be considered as being specifically disclosed.

Although the nucleotide sequences which encode CAPE and/or its variants are preferably capable of hybridizing to the nucleotide sequence of naturally occurring CAPE under stringent conditions, it may be advantageous to produce nucleotide sequences encoding CAPE or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding CAPE and/or its derivatives without altering the encoded aa sequence include the production of RNA transcripts having more desirable properties, such as a greater half-life, than transcripts produced from the naturally occurring sequence.

Nucleotide sequences encoding CAPE may be joined to a variety of other nucleotide sequences by means of well established recombinant DNA techniques (cf Sambrook J et al. supra). Useful nucleotide sequences for joining to cape include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for cape-specific nucleic acid hybridization probes capable of hybridizing with naturally occurring nucleotide sequences encoding CAPE. Such probes may also be used for the detection of similar serpin encoding sequences and should preferably contain at least 50% of the nucleotides from the conserved region or active site. The hybridization probes of the subject invention may be derived from the nucleotide sequences of SEQ ID NO 1 or from genomic sequences including promoters, enhancer elements and/or possible introns of respective naturally occurring CAPE molecules. Hybridization probes may be labeled by a variety of reporter groups, including radionuclides such as $^{32}$P or $^{35}$S, or enzymatic labels such as alkaline phosphatase coupled to the probe via avidin/biotin coupling systems, and the like.

Other means of producing specific hybridization probes for cape DNAs include the cloning of nucleic acid sequences encoding CAPE or CAPE derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding CAPE and their derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the cape sequences or any portion thereof.

PCR as described U.S. Pat. Nos. 4,683,195; 4,800,195; and 4,965,188 provides additional uses for oligonucleotides based upon the nucleotide sequence which encodes CAPE. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Full length genes may be cloned from known sequence using a new method which employs XL-PCR (Perkin-Elmer, Foster City, Calif.) to amplify long pieces of DNA. This method was developed to allow a single researcher to process multiple genes (up to 20 or more) at a time and to obtain an extended (possibly full-length) sequence within 6–10 days. It replaces current methods which use labelled probes to screen libraries and allow one researcher to process only about 3–5 genes in 14–40 days.

In the first step, which can be performed in about two days, primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones. If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg Md.). The cDNA library may have been prepared with oligo dT or random primers. The advantage of using random primed libraries is that they will have more sequences which contain 5' ends of genes. A randomly primed library may be particularly useful if an oligo dT library does not yield a complete gene. Obviously, the larger the protein, the less likely it is that the complete gene will be found in a single plasmid.

The nucleotide sequence can be used in an assay to detect conditions associated with altered expression of CAPE. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation, tumor and/or disease.

The nucleotide sequence for cape can be used to construct hybridization probes for mapping that gene. The nucleotide sequence provided herein may be mapped to a particular chromosome or to specific regions of that chromosome using well known genetic and/or chromosomal mapping techniques. These techniques include in situ hybridization, linkage analysis against known chromosomal markers, hybridization screening with libraries, flow-sorted chromosomal preparations, or artificial chromosome constructions YAC or P1 constructions. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of cape on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

Nucleotide sequences encoding CAPE may be used to produce purified CAPE using well known methods of recombinant DNA technology. Among the many publications that teach methods for the expression of genes after they have been isolated is Goeddel (1990) Gene Expression Technology, Methods and Enzymology, Vol 185, Academic Press, San Diego Calif. CAPE may be expressed in a variety of host cells, either prokaryotic or eukaryotic. Host cells may be from the same species in which cape nucleotide sequences are endogenous or from a different species. Advantages of producing CAPE by recombinant DNA technology include obtaining adequate amounts of the protein for purification and the availability of simplified purification procedures.

Cells transformed with DNA encoding CAPE may be cultured under conditions suitable for the expression of serpins and recovery of the protein from the cell culture. CAPE produced by a recombinant cell may be secreted or may be contained intracellularly, depending on the cape sequence and the genetic construction used. In general, it is more convenient to prepare recombinant proteins in secreted form. Purification steps vary with the production process and the particular protein produced.

In addition to recombinant production, fragments of CAPE may be produced by direct peptide synthesis using solid-phase techniques (cf Stewart et al (1969) Solid-Phase Peptide Synthesis, WH Freeman Co, San Francisco Calif.; Merrifield J (1963) J Am Chem Soc 85:2149–2154. In vitro protein synthesis may be performed using manual techniques or by automation. Automated synthesis may be achieved, for example, using Applied Biosystems 431A Peptide Synthesizer (Foster City, California Calif.) in accordance with the instructions provided by the manufacturer. Various fragments of CAPE may be chemically synthesized separately and combined using chemical methods to produce the full length molecule.

CAPE for antibody induction does not require biological activity; however, the protein must be immunogenic. Peptides used to induce specific antibodies may have an aa sequence consisting of at least five aa, preferably at least 10 aa. They should mimic an exposed portion of the aa sequence of the protein and may contain the entire aa sequence of a small naturally occurring molecule such as CAPE. Short stretches of CAPE aa may be fused with those of another protein such as keyhole limpet hemocyanin and the resulting chimeric molecule used for antibody production.

Antibodies specific for CAPE may be produced by inoculation of an appropriate animal with the polypeptide or an antigenic fragment. An antibody is specific for CAPE if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (Orlandi R et al (1989) PNAS 86:3833–3837, or Huse WD et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding CAPE.

An additional embodiment of the subject invention is the use of CAPE as a specific protease inhibitor to treat inflammatory or pathologic problems of the hypothalamus, or of a target tissue. A further embodiment of the subject invention is the use of CAPE to specifically bind a small molecule and to modulate its release either within the hypothalamus, a target tissue or extracellularly.

CAPE as a bioactive agent or composition may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving excess expression and activity of proteases. Alternatively, the compositions may be employed for treating problems associated with excessive levels of specific small molecules.

The examples below are provided to illustrate the subject invention. These examples are provided by way of illustration and are not included for the purpose of limiting the invention.

EXAMPLES

I Isolation of mRNA and Construction of cDNA Libraries

The hypothalamic library was constructed from a pooled sample of hypothalamic tissue taken from the normal human brains of 51 Caucasian males and females of different ages. The polyadenylated mRNA was obtained from Clontech Laboratories, Inc. (Catalogue No. #6579-2, Palo Alto Calif.)

The polyadenylated mRNA was used to construct a custom cDNA library (Stratagene, La Jolla Calif.). cDNA synthesis was primed using both oligo dT and random hexamers, and the two cDNA libraries produced were treated separately. Synthetic adapter oligonucleotides were ligated onto the cDNA enabling its insertion into the Stratagene Uni-ZAP™ vector system. This system allows high efficiency unidirectional (sense orientation) lambda library construction and the convenience of a plasmid system with blue/white color selection to detect clones with cDNA insertions. Finally, the two cDNA libraries were combined into a single library by mixing equal numbers of bacteriophage.

The hypothalamic cDNA library can be screened with either DNA probes or antibody probes and the pBluescript® phagemid (Stratagene) can be rapidly excised in vivo. The phagemid allows the use of a plasmid system for easy insert characterization, sequencing, site directed mutagenesis, creation of unidirectional deletions, and expression of fusion proteins. The custom-constructed library phage particles were infected into E Coli host strain XL1 Blue® (Stratagene) which has a high transformation efficiency. This efficiency increases the probability of obtaining rare, underrepresented clones in the cDNA library. Alternative unidirectional vectors include but are not limited to pcDNAI (Invitrogen, San Diego Calif.) and pSHlox-1 (Novagen, Madison Wis.).

II Isolation of CDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBluescript plasmid and the cDNA insert. The phagemid DNA was released from the cells and purified, then used to reinfect fresh bacterial host cells (SOLR, Stratagene Inc), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System® (QIAGEN Inc, Chatsworth Calif.). This technique provides a rapid and reliable high-throughput method for lysing the bacterial cells and isolating highly purified phagemid DNA. The DNA eluted from the purification resin was suitable for DNA sequencing and other analytical manipulations.

An alternate method of purifying phagemid has recently become available. It utilizes the Miniprep Kit (Catalog No. #77468, Advanced Genetic Technologies Corporation, Gaithersburg Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 μl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

III Sequencing of cDNA Clones

The cDNA inserts from random isolates of the hypothalamus library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 DNA sequencer).

IV Homology Searching of cDNA Clones and Deduced Proteins

Each sequence so obtained was compared to sequences in GenBank using a search algorithm developed by Applied Biosystems Inc. and incorporated into its INHERIT™ 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments of the protein sequence were used to display the results of the homology search.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul, SF (1993) J Mol Evol 36:290–300; Altschul, SF et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologues. Although it is ideal for matches which do not contain gaps, it is inappropriate for performing motif-style searching. The fundamental unit of BLAST algorithm output is the high-scoring segment pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Identification and Full Length Sequencing of the Genes

The nucleotide sequence for the entire coding region of the hypothalamus-derived serpin, CAPE, claimed in this invention is shown in FIG. 1. The cDNA of Incyte 84476 was extended to full length using a modified XL-PCR (Perkin Elmer) procedure. Primers were designed based on known sequence; one primer was synthesized to initiate extension in the antisense direction (XLR) and the other to extend sequence in the sense direction (XLF). The sequences of these primers and their location are as follows: XLR (nucleotides 502–525 in SEQ ID NO 1) and XLF (nucleotides 609–632 in SEQ ID NO 1). The primers allowed the sequence to be extended "outward" generating amplicons containing new, unknown nucleotide sequence for the gene of interest. The primers were designed using Oligo 4.0 (National Biosciences Inc, Plymouth Minn.) to be 22–30 nucleotides in length, to have a GC content of 50% or more, and to anneal to the target sequence at temperatures about 68°–72° C. Any stretch of nucleotides which would result in hairpin structures and primer primer dimerizations were avoided.

The hypothalamus cell cDNA library was used as a template, and XLR and XLF primers were used to extend and amplify the 84476 sequence. By following the instructions for the XL-PCR kit, the enzymes provided high fidelity in the amplification. Beginning with 25 pMol of each primer and the recommended concentrations of all other components of the kit, PCR was performed using the MJ PTC200 (MJ Research, Watertown Mass.) and the following parameters:

Step 1 94° C. for 60 sec (initial denaturation)
Step 2 94° C. for 15 sec
Step 3 65° C. for 1 min
Step 4 68° C. for 7 min
Step 5 Repeat step 2–4 for 15 additional cycles
Step 6 94° C. for 15 sec
Step 7 65° C. for 1 min
Step 8 68° C. for 7 min+15 sec/cycle
Step 9 Repeat step 6–8 for 11 additional cycles
Step 10 72° C. for 8 min
Step 11 4° C. (and holding)

At the end of 28 cycles, 50 µl of the reaction mix was removed; and the remaining reaction mix was run for an additional 10 cycles as outlined below:

Step 1 94° C. for 15 sec
Step 2 65° C. for 1 min
Step 3 68° C. for (10 min +15 sec)/cycle
Step 4 Repeat step 1–3 for 9 additional cycles
Step 5 72° C. for 10 min A 5∴ 10 µl aliquot of the reaction mixture was analyzed by electrophoresis on a low concentration, about 0.6–0.8%, agarose mini-gel to determine which reactions were successful in extending the sequence. Although all extensions potentially contain a full length gene, some of the largest products or bands were selected and cut out of the gel. Further purification involved using a commercial gel extraction method such as QIAQuick™ (QIAGEN Inc, Chatsworth Calif.). After recovery of the DNA, Klenow enzyme was used to trim single stranded, nucleotide overhangs creating blunt ends which facilitated religation and cloning.

After ethanol precipitation, the products were redissolved in 13 µl of ligation buffer. Then, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook J et al, supra). After incubation for one hour at 37° C., the whole transformation mixture was plated on Luria Bertani (LB)-agar (Sambrook J et al, supra) containing carbenicillin at 25 mg/L. The following day, 12 colonies were randomly picked from each plate and cultured in 150 al of liquid LB/carbenicillin medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 15 µl of PCA mix (1.33× containing 0.75 units of Taq polymerase, a vector primer and one or both of the gene specific primers used for the extension reaction) were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid and sequenced.

VI Antisense analysis

Knowledge of the cDNA sequence of the novel serpin gene will enable its use in antisense technology in the investigation of gene function. Oligonucleotides, genomic or cDNA fragments comprising the antisense strand of cape can be used either in vitro or in vivo to inhibit expression of the protein. Such technology is now well known in the art, and probes can be designed at various locations along the nucleotide sequence. By transfection of cells or whole test animals with such antisense sequences, the gene of interest can effectively be turned off. Frequently, the function of the gene can be ascertained by observing behavior at the cellular, tissue or organismal level (e.g. lethality, loss of differentiated function, changes in morphology, etc).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of CAPE

Expression of CAPE may be accomplished by subcloning the cDNAs into appropriate expression vectors and transfecting the vectors into appropriate expression hosts. In this particular case, the cloning vector used in the generation of the full length clone also provides for direct expression of the included cape sequence in E coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The cape cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae,* and bacteria such as *E. coli.* For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced CAPE can be recovered from the conditioned medium and analyzed using chromatographic methods known in the art.

VIII Isolation of Recombinant CAPE

CAPE may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen) between the purification domain and the cape sequence may be useful to facilitate expression of CAPE.

IX Production of CAPE Specific Antibodies

Two approaches are utilized to raise antibodies to CAPE, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of CAPE, as deduced from translation of the cDNA, is analyzed to determine regions of high immunogenicity. Oligopeptides comprising regions which are hydrophilic, highly antigenic, or highly likely to be on the serpin surface, as shown in FIG. 3, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled CAPE to identify those fusions producing the monoclonal antibody with the desired specificity. In a typical protocol, wells of plates (FAST; Becton-Dickinson, Palo Alto Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled CAPE, 1 mg/ml. Clones producing antibodies will bind a quantity of labeled CAPE which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ or stronger, will typically be made by standard procedures as described in Harlow and Lane (1988) Antibodies: A Laboratory Manual. Cold Spring Harbor Laboratory, Cold Spring Harbor N.Y.; and in Goding (1986) Monoclonal Antibodies: Principles and Practice, Academic Press, New York City, both incorporated herein by reference.

X Diagnostic Test Using CAPE Specific Antibodies

Particular CAPE antibodies are useful for the diagnosis of prepathologic conditions, and chronic or acute diseases which are characterized by differences in the amount or distribution of CAPE. To date, CAPE has only been found to be expressed in a hypothalamus library and thus may be specific for conditions that damage the hypothalamus and which can then be detected.

Diagnostic tests for CAPE include methods utilizing the antibody and a label to detect CAPE in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemilumine scent agents, chromogenic agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound CAPE, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on CAPE is preferred, but a competitive binding assay may be employed. These assays are described, among other places, in Maddox, Del. et al (1983, J Exp Med 158:121 1).

XI Purification of Native CAPE Using Specific Antibodies

Native or recombinant CAPE can be purified by immunoaffinity chromatography using antibodies specific for CAPE. In general, an immunoaffinity column is constructed by covalently coupling the anti-CAPE antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of CAPE by preparing a fraction from cells containing CAPE in a soluble form. This preparation is derived by solubilization of the whole cell or of a subcellular fraction obtained via differential centrifugation by the addition of detergent or by other methods well known in the art. Alternatively, soluble CAPE containing a signal sequence may be secreted in useful quantity into the medium in which the cells are grown.

A soluble CAPE-containing preparation is passed over the immunoaffinity column, and the column is washed under conditions that allow the preferential absorbance of serpin (eg, high ionic strength buffers in the presence of detergent). Then, the column is eluted under conditions that disrupt antibody/CAPE binding (e.g., a buffer of pH 2–3 or a high concentration of a chaotrope such as urea or thiocyanate ion), and CAPE is collected.

XII CAPE Activity

The activity of purified or expressed CAPE in protease inhibition may be tested by mixing a known quantity of the enzyme with a potential substrate protease such as chymotrypsin and a purified protein which chymotrypsin usually cleaves. The ability of a given amount of CAPE to inhibit chymotrypsin can be assayed by FPLC of the protein fragments produced under a given set of conditions in a specific period of time.

In another method to test CAPE activity as a protease inhibitor, a sample of the reaction materials may be run on a nondenaturing gel which separates the protease inhibitor complex, protease, inhibitor, protein substrate and protein fragments as different sized peptides.

The activity of purified or expressed CAPE in small molecule binding may be tested by incubating CAPE with various small molecules, preferably those derived from the hypothalamus or those that affect hypothalamus function, in radiolabeled form. After allowing a suitable time for binding, CAPE-bound small molecules may be separated from free small molecules by FPLC, and the binding affinity of CAPE for different small molecules determined.

XIII Rational Drug Design

The goal of rational drug design is to produce structural analogs of biologically active polypeptides of interest or of small molecules with which they interact, eg, inhibitors, agonists, antagonists, etc. Any of these examples can be used to fashion drugs which are more active or stable forms of the polypeptide or which enhance or interfere with the function of a polypeptide in vivo (Hodgson J (1991) Biotechnology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous serpin-like molecules, to identify efficient inhibitors, or to identify small molecules that may bind serpins. Useful examples of rational drug design may include molecules which have improved activity or stability as shown by Braxton S and Wells JA (1992 Biochemistry 31:7796–7801) or which act as inhibitors, agonists, or antagonists of native peptides as shown by Athauda SB et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the CAPE amino acid sequence provided herein will provide guidance to those employing computer modeling techniques in place of or in addition to x-ray crystallography.

XIV Use and Administration of CAPE

Since CAPE may be a protease inhibitor, it may be used to treat tissue wasting associated with excessive protease production during inflammation or diseases associated with nervous tissue degeneration. The tissues that may be affected by wasting may be the hypothalamus, where the serpin is expressed or tissues surrounding or adjacent to the hypothalamus. For example, neuronal loss in the NTL associated with diseases such as Kallmann's and Down's syndromes, or in Alzheimer's and Huntington's diseases may be prevented by administration of CAPE. Destruction of the posterior hypothalamus by ischemia, encephalitis, trauma or tumor may also be prevented.

On the other hand, CAPE may be a small molecule binding protein which can be used to modulate levels of specific small molecules in the treatment of disease. For example, anorexia, bulimia, depression, and some forms of diabetes may be related to the overproduction of one or more of the molecules, such as CRH, ACTH, TRH, TSH, GRH, GH, insulin, somatostatin, cholecystokinin, interleukins, oxytocin, insulin-like growth factors, glucagon, etc., which govern the nonendocrine intake and eating behaviors. CAPE may be employed to bind one of these molecules, thereby decreasing the symptoms of these diseases.

CAPE may also be used to decrease the amount of free circulating somatostatin to prevent somatostatin's inhibitory effect on the release of growth hormone. In another example, if CAPE were to remove excess levels of circulating prolactin, diseases such as galactorrhea and/or hypogandism may be avoided. Therefore, administration of CAPE may be useful to sequester some of these small molecules to prevent disease.

CAPE will be formulated in a nontoxic, inert, pharmaceutically acceptable aqueous carrier medium (CAPE treatment, CT) preferably at a pH of about 5 to 8, more preferably 6 to 8, although the pH may vary according to the characteristics of the formulation and its administration. Characteristics such as solubility of the molecule, half-life and antigenicity/immunogenicity will aid in defining an effective carrier. Native human proteins are preferred as CT, but recombinant, organic or synthetic molecules resulting from drug design may be equally effective in particular situations.

CTs may be delivered by known routes of administration including but not limited to transmucosal spray and aerosol, transdermal patch and bandage, intravenous formulations, orally administered liquids and pills particularly formulated to resist stomach acid and enzymes. For higher specificity in administration, CTs may be directly injected or implanted in the brain, close to the hypothalamus.

The particular formulation, exact dosage, and route of administration will be determined by the attending physician and will vary according to each specific situation. Such determinations are made by considering multiple variables such as the condition to be treated, the CT to be administered, and the pharmacokinetic profile of the particular CT. Additional factors which may be taken into account include disease state (e.g. severity) of the patient, age, weight, gender, diet, time of administration, drug combination, reaction sensitivities, and tolerance/response to therapy. Long acting CT formulations might be administered every 3 to 4 days, every week, or once every two weeks depending on half-life and clearance rate of the particular CT.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different uses of CT and that administration targeting a tissue or organ may necessitate delivery in a specific manner.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

We claim:

1. A diagnostic test for the detection of nucleotide sequences encoding and associated with excessive expression of CAPE serpin having the sequence of SEQ ID NO: 2 in a biological sample, the method comprising the steps of:

a) combining the biological sample with a first nucleotide sequence which comprises the nucleic acid sequence which encodes SEQ ID NO: 2 under conditions suitable for the formation of a nucleic acid hybridization complex; and b) detecting the hybridization complex, wherein the presence of the hybridization complex correlates with the presence of a second nucleotide sequence encoding CAPE serpin in the biological sample.

* * * * *